United States Patent [19]

Mayol et al.

[11] Patent Number: 4,618,680

[45] Date of Patent: * Oct. 21, 1986

[54] BENZANILIDE DERIVATIVE

[75] Inventors: Robert F. Mayol; Richard E. Gammans, both of Evansville, Ind.

[73] Assignee: Mead Johnson & Company, Evansville, Ind.

[*] Notice: The portion of the term of this patent subsequent to Jun. 1, 1999 has been disclaimed.

[21] Appl. No.: 325,166

[22] Filed: Nov. 27, 1981

Related U.S. Application Data

[63] Continuation of Ser. No. 188,184, Sep. 18, 1980, Pat. No. 4,332,803.

[51] Int. Cl.$^4$ ............................................. C07D 211/26
[52] U.S. Cl. ..................................... 546/234; 514/821
[58] Field of Search ........................................ 546/234

[56] References Cited

U.S. PATENT DOCUMENTS 3,931,195 1/1976 Dykstra et al. ..................... 546/234
4,318,899 3/1982 Mayol ................................. 546/234
4,332,803 6/1982 Mayol et al. ........................ 424/267

OTHER PUBLICATIONS

USAN and the USP Dictionary of Drug Names, 1980, p. 122, United States Pharmacopeial Convention, Inc., 12601 Twinbrook Parkway, Rockville, Md., 20852.
S. J. Dykstra et al, Jour. Med. Chem. (1973) vol. 16, No. 9, pp. 1015-1020.
R. F. Mayol et al, Therap. Drug Monitoring (1979) vol. 1, pp. 507-524.
J. E. Byrne et al, Jour. Pharm. and Exper. Therap. (1977) 200, pp. 147-154.
V. Elharrar et al, J. Pharmacol. Exp. Ther. (1982) 220, pp. 440-447.

*Primary Examiner*—Norma S. Milestone
*Attorney, Agent, or Firm*—Robert H. Uloth; Robert E. Carnahan

[57] ABSTRACT

4-Hydroxy-3-methoxy-N-[2-[2-(1-methyl-2-piperidinyl)ethyl]-phenyl]benzamide is an antiarrhythmic agent having relatively low toxicity and increased duration of action.

1 Claim, No Drawings

BENZANILIDE DERIVATIVE

This application is a continuation of application Ser. No. 188,184, filed Sept. 18, 1980, now U.S. Pat. No. 4,332,803.

FIELD OF THE INVENTION

4-Hydroxy-3-methoxy-N-[2-[2-(1-methyl-2-piperidinyl)ethyl]phenyl]benzamide is a heterocyclic carbon compound of the piperidine series having an additional ring and having nitrogen attached indirectly to the piperidine ring by non-ionic bonding.

SUMMARY OF THE INVENTION

This invention is concerned with the 4-hydroxy-3-methoxybenzanilide analog of encainide which has the following structural formula.

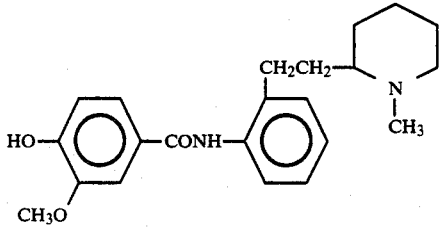

This substance is a metabolite in man of encainide and an improved antiarrhythmic agent with regard to its extended duration of action relative to encainide.

DESCRIPTION OF THE PRIOR ART

Encainide hydrochloride is an antiarrhythmic compound which is also referred to in the literature as MJ 9067 (USAN And The USP Dictionary of Drug Names 1980, page 122, United States Pharmacopeial Convention, Inc., 12601 Twinbrook Parkway, Rockville, MD 20852, Library of Congress Catalog Card No. 72-88571). Encainide has the following structural formula.

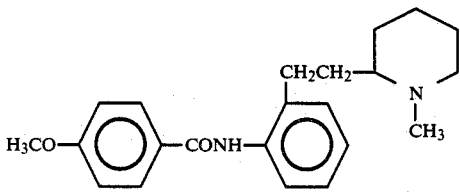

The following publications describe the chemical synthesis of encainide, a number of analogs thereof, and the antiarrhythmic properties of these compounds in animals.

Dykstra, et al., J. Med. Chem., 16, 1015–1020 (1973).

Dykstra and Minielli, U.S. Pat. No. 3,931,195 patented Jan. 6, 1976.

Byrne, et al., J. Pharmacology and Experimental Therapeutics, 200, 147–154 (1977).

Assay methods for encainide and its metabolites are disclosed in the following references.

Mayol and Gammans, Therap. Drug Monitoring, 1, 507–524 (1979).

Mayol, U.S. patent application Ser. No. 155,338 filed June 2, 1980.

DETAILED DESCRIPTION OF THE INVENTION

The structures of encainide and a number of analogs thereof which are described in the foregoing Dykstra, et al. publication and patent are shown in the following table in comparison to the structure of the compound of the present invention. The compound numbers used in the table are the same as the example numbers employed in the Dykstra, et al. patent. Compound No. A is the compound of the present invention.

Structures

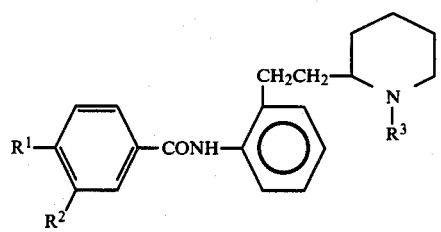

| Compound No. | | $R^1$ | $R^2$ | $R^3$ |
|---|---|---|---|---|
| 89 | (O—demethylencainide, or ODE) | HO— | H— | $CH_3$— |
| 107 | (encainide, or E) | $CH_3O$— | H— | $CH_3$— |
| 108 | | H— | $CH_3O$— | $CH_3$— |
| 109 | | $CH_3O$— | $CH_3O$— | $CH_3$— |
| 139 | (N—demethylencainide, or NDE) | $CH_3O$— | H— | H— |
| A | (3-methoxy-O—demethylencainide, or 3-methoxy ODE) | HO— | $CH_3O$— | $CH_3$— |

Compound Nos. 89 and 139 have been identified by Mayol and Gammans (op. cit.) as metabolites of encainide (Compound No. 107) in which publication the former is referred to as ODE and the latter is NDE. The former (CDE) has been identified as a principal metabolite which is sometimes present in plasma in amounts several times the concentration of encainide following treatment with the latter. As a result of an improvement of the high pressure liquid chromatography assay method described in the Mayol and Gammans publication, which improvement constitutes part of the present invention, it has been found that Compound A is also a principal metabolite of encainide in man following oral administration of the latter, and that it is present in concentrations in the blood plasma substantially greater than that Compond No. 89 two or more hours following the administration of a 50 mg. dose of encainide hydrochloride orally. The HPLC assay method described in the Mayol and Gammans publication has now been found to have been incapable of distinguishing between Compound Nos. 89 and Compound A. It is thought that Compound A is produced in the body from Compound No. 89 by a biological transformation process.

For comparative purposes the biological activity of the compounds whose structures are shown in the above table are presented in the following table in which comparative antiarrhythmic activity is given as determined by the laboratory screening test referred to in the Dykstra, et al. paper above. This is referred to in the table as Test I. Test II is an approximation of the oral toxicity of these compounds in mice, and Tests III and IV refer to the human metabolism results observed following oral administration of an antiarrhythmic oral dose of 75 mg/kg of encainide hydrochloride to patients.

Biological Activity

I. Antiarrhythmic activity for ventricular arrhythmia in mice produced by chloroform inhalation; $ED_{50}$ expressed as mg/kg body weight, intraperitoneal administration, J. W. Lawson, J. Pharmacol. Expt. Ther. 160, 22 (1968).
II. $ALD_{50}/ATD_{50}$ mouse treated orally; $ALD_{50}$ is the approximate lethal dose for half the animals; $ATD_{50}$ is the approximate lowest dose where signs of physiologic or neurologic deficit appear in half the animals, expressed as mg/kg body weight.
III. Time following oral dosing of humans with 75 mg. of encainide hydrochloride for clearance (plasma concentration <20 ng./ml.) from blood plasma; hours.
IV. Approximate half life in human blood plasma following oral dosing with encainide hydrochloride; hours.

| Compound No. | I | II | III | IV |
|---|---|---|---|---|
| 89 | 1.7–2.8* | 25–50/5–10 | >16 | 4–6 |
| 107 (encainide) | 5.3–15* | 50–100/5–10 | 6 | 2.5–3 |
| 108 | 10 | 100/10–25 | ** | ** |
| 109 | 10 | 100/25 | ** | ** |
| 139 | 28 | 147/15.7 | + | + |
| A | 9.5 | 250/31.3–62.5 | >16 | 4–6 |

*Range of various determinations.
**Compounds have not been administered to man nor observed as metabolites of encainide in man or animals.
+Occurrence in plasma following oral administration of encainide to man has been rare, and value has not been determinable.

The foregoing results reflect approximately equivalent antiarrhythmic activity for each of these substances except for Compound No. 89 which is somewhat more potent but also somewhat more toxic in mice. Compound A differs from and enjoys the advantages over each of Compound Nos. 89 and 107 of reduced toxicity and of a more prolonged presence in the blood.

DESCRIPTION OF SPECIFIC EMBODIMENTS

EXAMPLE 1

Assay Procedure

A. Extraction of Biological Fluid

To 1 ml of plasma or urine in a screw-capped tube there is added 0.2 ml of 0.5M. Tri-HCl buffer (2-amino-2-hydroxymethyl-1,3-propanediol), pH 8.5, and 10 ml of n-butyl chloride containing 5% by volume of isopropanol. The sample is then shaken on an oscillating mixer followed by centrifugation to separate the phases. A 9 ml aliquot of the organic layer is removed and evaporated to dryness under a stream of nitrogen and the residue is redissolved in 100 mcl of ethanol. A 50 mcl aliquot of this solution is injected onto the column for high pressure liquid chromatography.

B. High Pressure Liquid Chromatography (HPLC) Conditions

A normal phase silicic acid column having dimensions 3.9 mm by 30 cm in length equipped with a variable wavelength UV detector set at 254 nm is used. The mobil phase employed consists of 500 ml of ethanol, 30 ml of water, and 0.1 ml of methanesulfonic acid at a flow rate of 1 ml per minute. A series of standards containing 0, 25, 100 and 500 ng/ml of each compound to be assayed was prepared using pooled human plasma. These standards were treated as described above. Quantification of the detector response was achieved by digital integration or measurement of peak heights. The standard curve for each component was constructed by linear regression of the detector response versus concentration from the plasma standards. The concentration of compound in the sample was then interpolated from these curves.

C. Results

The relative order of elution of encainide and its O-demethyl and 3-methoxy O-demethyl metabolites from the column and their retention times is as follows: Compound No. 89, 8.3 minutes; Compound A, 9.7 minutes; Compound No. 107, 11.4 minutes. The last endogenous plasma component eluted from the column has a retention time of 3.6 minutes and the baseline is very stable in the region where the metabolites elute. Thus, no interference from endogenous plasma components occurs. Due to differences in extraction efficiencies, specific molar absorptivities, and retention times for the individual components, the sensitivity of the assay for each of these components is as follows: Compound No. 89, 10 ng/ml; Compound A, 20 ng/ml; Compound No. 107, 15 ng/ml.

EXAMPLE 2

Synthesis of 4-Hydroxy-3-methoxy-N-[2-[2-(1-methyl-2-piperidinyl)ethyl]phenyl]benzamide (Compound A, 3-Methoxy ODE)

(1) Salt With Mucic Acid

A solution of 7.3 g (0.033 mole) of 2-(2-aminophenethyl)-1-methylpiperidine in 65 ml of pyridine is treated at ice bath temperature with 9.3 g (0.034 mole) of 4-benzyloxy-3-methoxybenzoylchloride in 30 ml of tetrahydrofuran. The reaction mixture is stirred for 1 hr at room temperature and then volatile materials removed by concentration in vacuo to yield an oil. The latter is dissolved in chloroform, washed with dilute aqueous sodium hydroxide water, brine, and then dried over magnesium sulfate. The dried solution is treated with activated carbon and concentrated in vacuo to an oil weighing 10.23 g which is shown to contain only one component by thin layer chromatography. This material is then dissolved in 100 ml of absolute ethanol and catalytically reduced in a low pressure hydrogenation apparatus over 2 g of 10% palladium on carbon catalyst at 60 psig until one molecular proportion of hydrogen has been absorbed. The catalyst is removed by filtration and the solvent distilled in vacuo to yield the product in free base form as a foam-like solid. Conversion to the mucate salt is achieved by triturating the residue with hot hexane to yield 5.3 g of a granular solid. The latter is dissolved in warm absolute ethanol and treated with 0.45 molecular equivalents of mucic acid to yield the hemimucate salt which is recrystallized from a mixture of absolute ethanol and ethyl acetate, m.p. 110°–165°.

Anal: C, 62,58; H, 6.89; N, 5.75; $H_2O$, 2.18. The composition corresponds to the monohydrate of the hemimucate salt.

IR: 760, 1290, 1450, 1505, 1605, 1635, 1770, 2940, and 3400 $cm^{-1}$.

HNMR (DMSO-$d_6$): 1.55 (10, m), 2.35 (3, s), 2.65 (3, m), 3.84 (3, s), 4.12 (2, m), 6.88 (1, d, 8.0 Hz), 7.25 (5, m), 7.54 (1, m), 9.80 (1, bs).

(2) Free Base

The foam-like solid free base above is dissolved in acetone and decanted from insoluble material. The filtrate is diluted with hexane and concentrated by boiling off the solvent until a light tan colored solid is formed which is collected. Purification of a portion of the tan colored solid by column chromatography on alumina using chloroform containing 5% by volume of methanol for development yielded material m.p. 135°–136° which was indistinguishable from the original by analysis.

Anal: C, 71,78; H, 7.68; N, 7.48.

IR: 760, 1215, 1290, 1450, 1505, 1585, 1640 and 2940 $cm^{-1}$.

NMR (CDCl$_3$): 1.20 (6, m), 1.90 (4, m), 2.22 (3, s), 2.70 (3, m), 3.90 (3, s), 6.00 (1, bs), 6.89 (1, d, 8.2 Hz), 7.22 (4, m), 7.52 (1, d, 1.8 Hz), 8.08 (1, m), 1.48 (1, bs).

The HNMR spectrum of this material was identical with that of the metabolite isolated from plasma and urine samples by the HPLC assay procedure described above.

The compound of the present invention and its pharmaceutically acceptable salts may be used for therapeutic purposes and particularly for the treatment of cardiac arrhythmias in much the same way and in similar dosage amounts as encainide. Dosage at longer intervals than is necessary with encainide is suitable as is indicated by the relative plasma half-lives of the two compounds. Dosage may be by the oral or parenteral routes including intramuscular, intraperitoneal, subcutaneous and intravenous, the latter being the preferred of the parenteral routes. For normal therapeutic purposes in the prevention or treatment of arrhythmias, oral administration is preferred. Generally, treatment is commenced with a unit dose smaller than anticipated for optimum control of the arrhythmia. Thereafter, the dosage is increased by small increments until the optimal effect is reached. Smaller dosage units are generally required for intravenous treatment than are required for oral treatment. The dosage amount administered is preferably at an effective level which is without harmful or deliterous side effect on the patient.

The compounds are ordinarily administered in combination with a pharmaceutical carrier. The nature and proportion of carrier is determined by the chosen route of administration and by the normal practices of pharmaceutical science. They may be administered orally in the form of tablets, coated tablets, or capsules containing excipients such as starch, lactose, sugar, various pharmaceutical clays, gelatin, stearic acid or salts thereof, vegetable fats or oils, gums, glycols and other known excipients. For parenteral administration sterile solutions are preferred.

The normal dosage range is from 0.01 to 20 mg/kg of body weight of the mammal under treatment. Fixed dosage units containing from 1 to 500 mg and preferably from 5 to 100 mg of the active ingredient are preferred.

EXAMPLE 3

Pharmaceutical Compositions

The compounds of the present invention are formulated with pharmacologically acceptable carriers to provide compositions useful in the present invention. Typical of the pharmaceutical compositions are the following:

| A. Tablets | |
|---|---|
| Material | Amount |
| Compound A (Example 2), as the base | 50.0 g |
| Magnesium stearate | 1.3 g |
| Corn starch | 12.4 g |
| Corn starch pregelatinized | 1.3 g |
| Lactose | 185.0 g |

The foregoing materials are blended in a twin-shell blender and then granulated and pressed into tablets weighing 250 mg. each. Each tablet contains 50 milligrams of active ingredient. The tablet may be scored in quarters so that a dose of 12.5 mg. of active ingredient may be conveniently obtained.

| B. Capsules | |
|---|---|
| Material | Amount |
| Compound A (Example 2), as the base | 125.0 mg |
| Lactose | 146.0 mg |
| Magnesium stearate | 4.0 mg |

The foregoing materials are blended in a twin-shell blender and then filled into No. 1 hard gelatin capsules. Each capsule contains 125 mg of active ingredient.

C. Solution for Intravenous Administration

A sterile solution suitable for intravenous injection is prepared by dissolving 10.0 g of Compound A (Example 2) as the base in a minimal amount of 0.5N hydrochloric acid. This solution is adjusted to pH 4.3 with 0.1N sodium hydroxide and diluted to 1000 ml total volume with physiologic saline solution. The solution is sterilized by passage through a bacteriological filter and aseptically filled into 10 ml sterile ampoules. Each milliliter of solution contains 10 mg of the active ingredient.

What is claimed is:

1. 4-Hydroxy-3-methoxy-N-[2-[2-(1-methyl-2-piperidinyl)ethyl]phenyl]benzamide.

* * * * *